(12) United States Patent
Menzel

(10) Patent No.: US 9,554,756 B2
(45) Date of Patent: Jan. 31, 2017

(54) SYSTEMS AND METHODS FOR CUSTOMIZING A MULTIPLE ALARM SYSTEM IN A PORTABLE PATIENT MONITOR

(75) Inventor: Frank Menzel, Oakland, NJ (US)

(73) Assignee: SHENZHEN MINDRAY BIO-MEDICAL ELECTRONICS CO. LTD., Shenzhen (CN)

(*) Notice: Subject to any disclaimer, the term of this patent is extended or adjusted under 35 U.S.C. 154(b) by 1210 days.

(21) Appl. No.: 12/638,821

(22) Filed: Dec. 15, 2009

(65) Prior Publication Data
US 2011/0140896 A1   Jun. 16, 2011

(51) Int. Cl.
*A61B 5/00* (2006.01)
*A61B 5/0205* (2006.01)
*G06F 19/00* (2011.01)

(52) U.S. Cl.
CPC ........ *A61B 5/746* (2013.01); *A61B 5/02055* (2013.01); *G06F 19/3406* (2013.01); *G06F 19/3418* (2013.01)

(58) Field of Classification Search
CPC . A61B 5/746; A61B 5/02055; G06F 19/3406; G06F 19/3418

USPC .................................. 340/500, 540, 573.1
See application file for complete search history.

(56) References Cited

U.S. PATENT DOCUMENTS

| | | | | |
|---|---|---|---|---|
| 3,972,320 A | * | 8/1976 | Kalman | A61B 5/0002 128/903 |
| 5,724,025 A | * | 3/1998 | Tavori | A61B 5/0002 340/573.1 |
| 2004/0249249 A1 | * | 12/2004 | Lawson | A61B 5/02405 600/300 |

* cited by examiner

*Primary Examiner* — James Yang
(74) *Attorney, Agent, or Firm* — Kory D. Christensen; Stoel Rives LLP

(57) ABSTRACT

A patient monitoring system allows medical personnel to customize multi-parameter alarms for particular patients and/or medical conditions. A patient monitor provides a user interface that allows medical personnel to create custom alarms by selecting patient parameters, desired levels or limits, comparators, and logic connectors to define an alarm condition that includes boundary conditions for a plurality of different patient parameters. A user may also link or group the different boundary conditions to define an order in which to process the various logic connectors.

22 Claims, 12 Drawing Sheets

SYSTEMS AND METHODS FOR CUSTOMIZING A MULTIPLE ALARM SYSTEM IN A PORTABLE PATIENT MONITOR

TECHNICAL FIELD

The present disclosure relates to patient monitor systems.

BRIEF SUMMARY

A patient monitoring system according to one embodiment allows medical personnel to customize multi-parameter alarms for particular patients and/or medical conditions. A patient monitor provides a user interface that allows medical personnel to create custom alarms by selecting patient parameters, desired levels or limits, comparators, and logic connectors to define an alarm condition that includes boundary conditions for a plurality of different patient parameters. A user may also link or group the different boundary conditions to define an order in which to process the various logic connectors.

Additional aspects will be apparent from the following detailed description, which proceeds with reference to the accompanying drawings.

DETAILED DESCRIPTION

Figure 1:
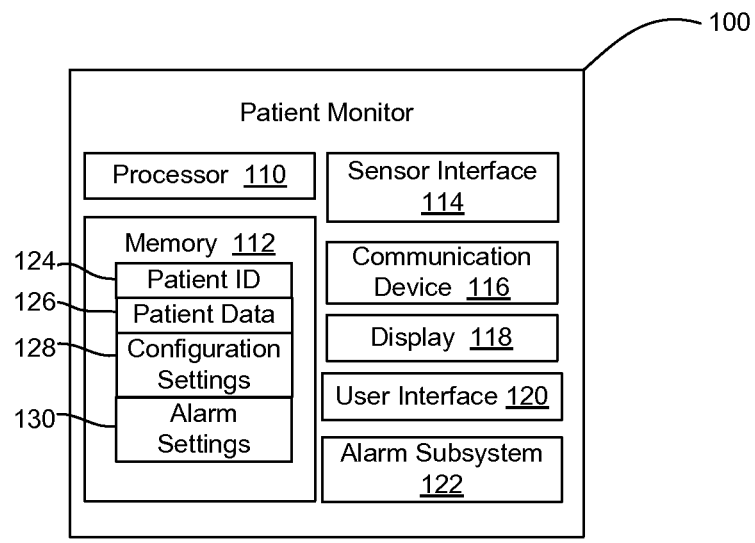
FIG. 1 is a block diagram of a patient monitor according to one embodiment.

Patient monitors are used to acquire, analyze, and display data from sensors attached to a patient. It is often desirable to set alarms to notify a user (e.g., doctor, nurse, or other medical personnel) that one or more monitored patient parameters are outside of a desired range. Generally, a user may enter limit values into a patient monitor for a particular alarm. However, alarm systems typically do not allow for user-customization of advanced alarm conditions based on desired combinations of patient parameters.

Thus, certain embodiments disclosed herein allow medical personnel to customize multi-parameter alarms for particular patients and/or medical conditions. A patient monitor provides a user interface that allows medical personnel to create custom alarms by selecting patient parameters (e.g., pulse, temperature, respiration, blood pressure, blood oxygen, electrocardiogram, and other monitored data), desired levels or limits, comparators (e.g., equal, less than, less than or equal, greater than, greater than or equal), and logic connectors (e.g., Boolean logic connectors such as "and," "or," and "not") to define an alarm condition that includes boundary conditions for a plurality of different patient parameters. In certain embodiments, a user may also link or group the different boundary conditions (e.g., nesting) to define an order in which to process the various logic connectors. A user may, for example, customize an alarm for a patient that may become septic that includes boundary conditions for temperature, respiration, heart rate, and blood pressure.

In certain embodiments, the user may also define data processing used for the boundary conditions corresponding to respective patient parameters. For example, rather than merely comparing a measured temperature value with a user-defined temperature range, the user may specify that the temperature data collected over a user-defined period of time undergo statistical analysis (e.g., to determine an average, mean, or other statistical value) before being compared to the user-defined limit. Further, the user may define a time constant that specifies an interval over which the measured values corresponding to a particular patient parameter exceeds a limit before triggering the alarm. For example, the user may specify that the patient's body temperature should remain at or above 101° F. for at least 10 minutes before triggering the alarm. The user may also specify that the limit of a particular parameter is based on a rate of change, rather than an instantaneous value. An artisan will recognize from the disclosure herein that the user may define other data manipulations or time periods to create customized alarm conditions.

In addition, or in other embodiments, default alarm profiles are provided that are associated with particular medical conditions, particular hospital wards or units, particular medical personnel preferences, and/or industry standards. The user may implement and/or modify the default alarm profiles. The user may also save modified or newly created alarm profiles for use with a patient monitor used to create the alarm profile and/or with other patient monitors.

In one embodiment, a method for monitoring a patient using user-customizable alarm profiles in a patient monitor system includes providing a user interface to a user of the patient monitor system, receiving (through the user interface) a first boundary condition associated with a first patient parameter, and receiving (through the user interface) a second boundary condition associated with a second patient parameter. The method also includes receiving (through the user interface) a first logic connector that relates the first boundary condition to the second boundary condition to define an alarm condition, measuring values of the first patient parameter and the second patient parameter, and triggering an alarm based on a comparison of the measured values with the defined alarm condition.

In one embodiment, receiving the first boundary condition includes receiving a selection of a first comparator from among a plurality of available comparators, and receiving a selection of a first limit value associated with the first patient parameter and the first comparator. Receiving the first boundary condition may further include receiving a selection of a second comparator from among the plurality of available comparators, and receiving a selection of a second limit value associated with the first patient parameter and the second comparator.

In another embodiment, the method further includes receiving a third boundary condition associated with a third patient parameter, and receiving a second logic connector that relates the third boundary condition to at least one of the first boundary condition and the second boundary condition to further define the alarm condition. The method may further include receiving an indication of a link between at least one of the first boundary condition, the second boundary condition, and the third boundary condition. The link defines an order in which to process the first logic connector and the second logic connector to determine an occurrence of the defined alarm condition.

In another embodiment, receiving the first boundary condition includes receiving a limit value and a time constant. The time constant defines an interval over which the measured values of the first patient parameter exceeds the limit value before triggering the alarm. In addition, or in other embodiments, receiving the first boundary condition may include receiving a limit value defining a rate of change for the first patient parameter and/or receiving a limit value and an indication of a statistical operation that defines an analysis to perform on the measured values of the first patient parameter.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or detailed description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform the processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/computer-readable medium suitable for storing electronic instructions.

FIG. 1 is a block diagram of a patient monitor 100 according to one embodiment. The patient monitor 100 includes a processor 110, a memory device 112, a sensor interface 114, a communication device 116, a display 118, a user interface 120, and an alarm subsystem 122. The processor 110 is configured to process patient data signals received through the sensor interface 114 and to display the patient data signals (e.g., as waveforms and/or numerical readouts) on the display 118. The sensor interface 114 receives the patient data signals from one or more sensors (not shown) attached to a patient (not shown). The sensor interface 114 may be configured to process the acquired patient data signals in cooperation with the processor 110.

The patient monitor 100 may store the patient data signals in the memory device 112 along with other data. For example, the patient monitor 100 may store a patient identifier) 12(ID 4 corresponding to a particular patient, patient data 126 corresponding to the patient data signals, configuration settings 128 (discussed below) for the patient monitor 100, alarm settings 130, and/or other data in the memory device 112.

The communication device 116 is configured to communicate, for example, with a network (not shown). In certain embodiments, the communication device 116 is also configured to wirelessly communicate with the network when the patient monitor 100 is being transported within a hospital.

In certain embodiments described herein, the display 118 is configured to display the user interface 120 to allow a user to create customized, multi-parameter alarms. Various example user interfaces 120 are described in detail below. An artisan will recognize from the disclosure herein, however, that many different types of configurations may be used for the user interface 120. In certain embodiments, the user interface 120 is generated by the alarm subsystem 122. In certain embodiments, the alarm subsystem 122 presents the user with available options or lists through the user interface 120. The alarm subsystem 122 then generates custom alarms from user-selections received through the user interface 120 for patient parameters, limits, comparators, logic connectors, links, time constants, data processing, and/or other alarm configurations.

An artisan will recognize from the disclosure herein that the alarm subsystem 122 and/or the sensor interface 114 may be combined with the processor 110 into a single unit. Further, the processor 110, sensor interface 114, and/or alarm subsystem 122, either combined or separately, may include a special purpose processor configured to perform the processes described herein. In another embodiment, the processor 110, sensor interface 114, and/or alarm subsystem 122, either combined or separately, may include a general purpose processor configured to execute computer-executable instructions (e.g., stored in a computer-readable medium such as the memory device 112) to perform the processes described herein.

Figure 2:
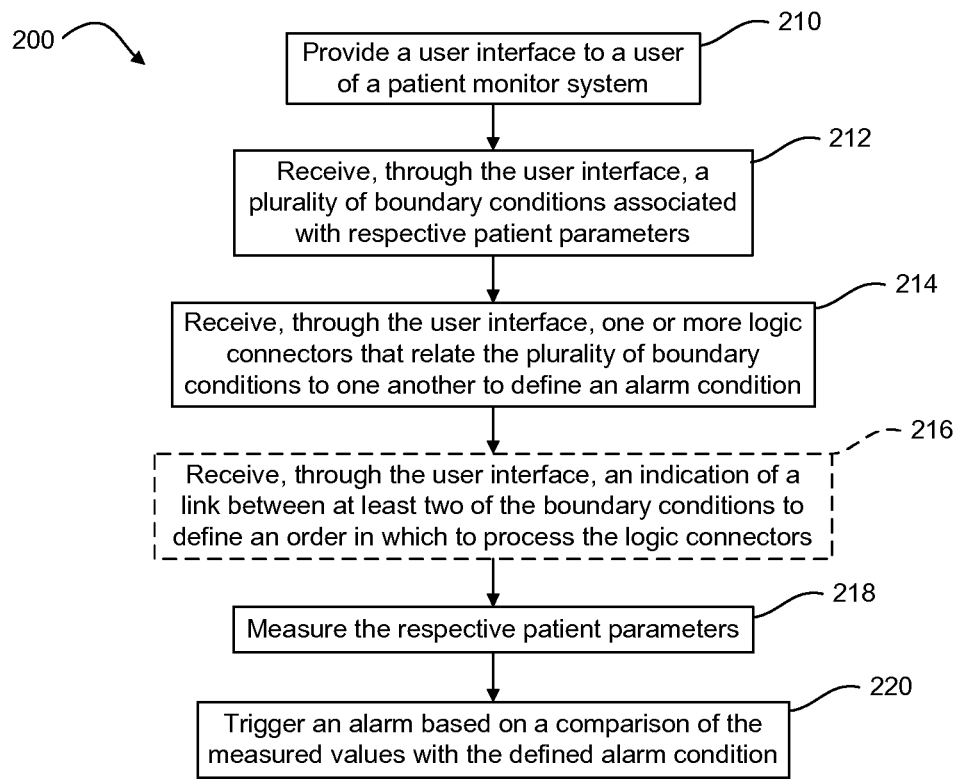
FIG. 2 is a flowchart of a process for monitoring a patient using a user-customized alarm according to one embodiment.

FIG. 2 is a flowchart of a process 200 for monitoring a patient using a user-customized alarm according to one embodiment. The process 200 may be performed, for example, by the patient monitor system 100 shown in FIG. 1. With reference to FIG. 1 and FIG. 2, the process 200 includes providing 210 a user interface 120 to a user of a patient monitor system 100.

The process 200 further includes receiving 214, through the user interface 120, a plurality of boundary conditions associated with respective patient parameters. As discussed above, the patient parameters may include, for example, pulse, temperature, respiration, blood pressure, blood oxygen, electrocardiogram, and other monitored data. In some embodiments, the alarm subsystem 122 receives a selection of patient parameters for each boundary condition from among a plurality of available patient parameters presented to the user through the user interface 120. Receiving 212 a particular boundary condition may include receiving a selection of one or two comparators from among a plurality of available comparators presented to the user through the user interface, and receiving a selection of limit values associated with the selected patient parameter and the selected comparators.

In one embodiment, receiving 212 a particular boundary condition may include receiving a limit value and a time constant, wherein the time constant defines an interval over which the measured values of the first patient parameter exceeds the limit value before triggering the alarm. In another embodiment, receiving 212 a particular boundary condition includes receiving a limit value defining a rate of change for the corresponding patient parameter. In still another embodiment, receiving 212 a particular boundary condition may include receiving a limit value and an indication of a statistical operation, wherein the statistical operation defines an analysis to perform on the measured values of the first patient parameter.

The process 200 further includes receiving 214, through the user interface 120, one or more logic connectors that relate the plurality of boundary conditions to one another to define an alarm condition. In one embodiment, the logic connectors are Boolean logic connectors. For example, the logic connector "and" may be selected by the user to signify that both of the connected boundary conditions (e.g., A and B) are exceeded to trigger the alarm. As another example, the logic connector "or" may be selected by the user to signify that alarm will be triggered if either of the connected boundary conditions (e.g., A or B) is exceeded. Other Boolean logic connectors known to those of skill in the art may also be used.

As indicated by the dashed line in FIG. 2, in some embodiments the process 200 also includes receiving 216, through the user interface 120, an indication of a link between at least two of the boundary conditions to define an order in which to process the logic connectors. For example, for three boundary conditions A, B, C, the user may select logic connectors to specify the expression:

$$A \text{ and } B \text{ or } C. \tag{1}$$

If the logic connectors are executed in order from left to right, then expression (1) indicates that the alarm is triggered if both boundary conditions A and B are exceeded, or the alarm is triggered if boundary condition C alone is exceeded. Alternatively, the user may link boundary conditions B and C to specify the expression:

$$A \text{ and } (B \text{ or } C), \tag{2}$$

which includes parenthesis to indicated that the "or" connector is executed before the "and" connector. In expression (2), boundary conditions B and C may be considered to be "nested" as a single condition. Thus, expression (2) indicates that the alarm is triggered if boundary condition A is exceeded, as long as either boundary condition B or C is also exceeded.

The process 200 further includes measuring 218 the respective patient parameters using the patient monitor 100, and triggering 220 an alarm based on a comparison of the measured values with the defined alarm conditions.

FIGS. 3A, 3B, 3C, 3D, 3E, and 3F graphically represent a user interface 300 for allowing a user of a patient monitor system to create a custom alarm according to one embodiment. In short, FIGS. 3A, 3B, 3C, 3D, 3E, and 3F illustrate an example progression of displayed options and user-selections to define multiple boundary conditions and to relate the boundary conditions to define an alarm condition. In this example embodiment, the number of displayed boundary conditions increases as the user adds additional patient parameters to define the alarm condition.

Figure 3A:
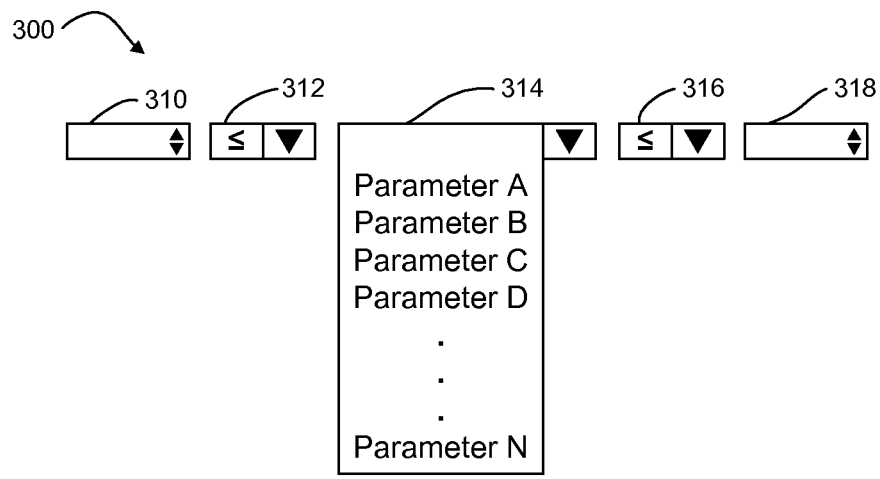
FIGS. 3A, 3B, 3C, 3D, 3E, and 3F graphically represent a user interface for allowing a user of a patient monitor system to create a custom alarm according to one embodiment.
Figure 3B:
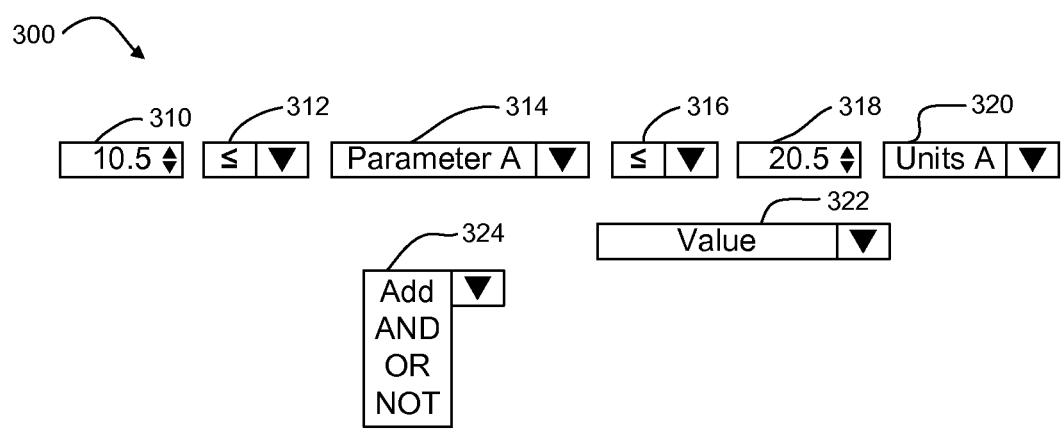

In FIGS. 3A and 3B, the user interface 300 displays various user-selectable fields associated with a first boundary condition, including a first limit field 310, a first comparator field 312, a parameter field 314, a second comparator field 316, and a second limit field 318. The comparator fields 312, 314 allow the user to select from a plurality of comparators including, for example, equal to ($=$), less than ($<$), less than or equal to ($\leq$), greater than ($>$), and greater than or equal to ($\geq$). In this example, the user selects the first and second comparator fields 312, 316 to be less than or equal to ($\leq$). The parameter field 314 allows the user to select a patient parameter from a list of available patient parameters that are monitored by the patient monitor 122. As shown in FIG. 3A, the parameter field 314 in this example lists Parameters A, B, C, D, . . . , N, which generically represent any type of patient parameter.

As shown in FIG. 3B, the user selects parameter A and enters numeric values for the first and second limit fields 310, 318 to create the following expression for the first boundary condition:

$$10.5 \leq \text{Parameter A} \leq 20.5. \tag{3}$$

As also shown in FIG. 3B, selection of Parameter A from the parameter field 314 causes the display of a units field 320, a function field 322, and a logic connector field 324. The units field 320 allows the user to select appropriate units corresponding to the selected parameter.

The function field 322 allows the user to select any processing performed on the monitored data for the selected parameter to further define the boundary condition. For example, the function field 322 may include options for a value, an average, a mean, a rate of change, or an interval (see FIG. 3D). As shown in FIG. 3B, the user in this example selects "value" for the function field 322 to indicate that each measured value of Parameter A is evaluated to determine whether it satisfies the conditions of expression (3), as specified by the fields 310, 312, 314, 316, 318, and 320. As another example, the user may decide to take the average or mean of the measured values of Parameter A (e.g., over a predetermined or user-defined time period). In this situation, the calculated average or mean value would be evaluated to determine whether it satisfies the conditions of expression (3). An artisan will recognize from the disclosure herein that the disclosed embodiments are not limited to average or mean values, and that other statistical or mathematical processing may be performed on the collected patient data.

Figure 3C:
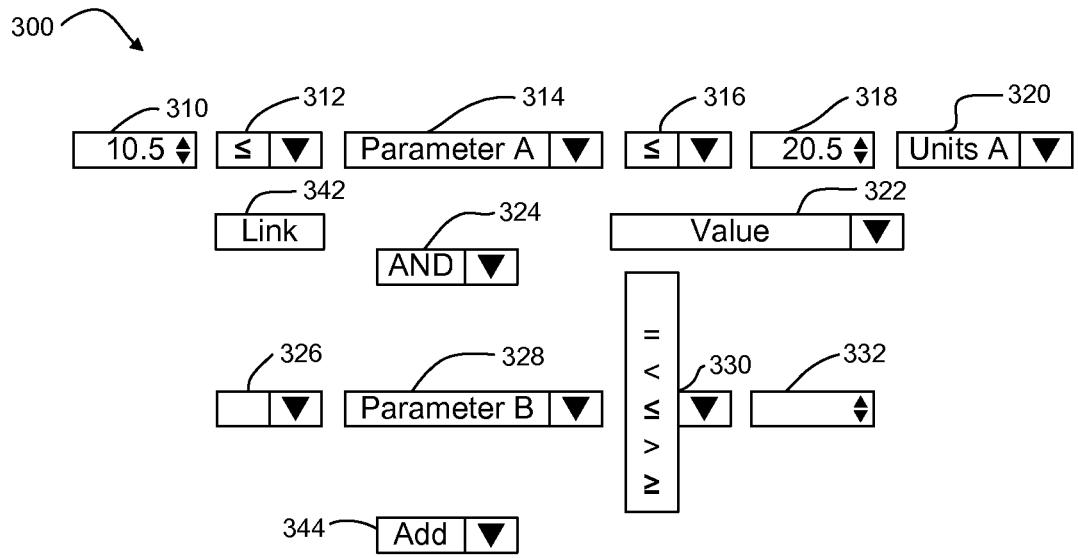
Figure 3D:
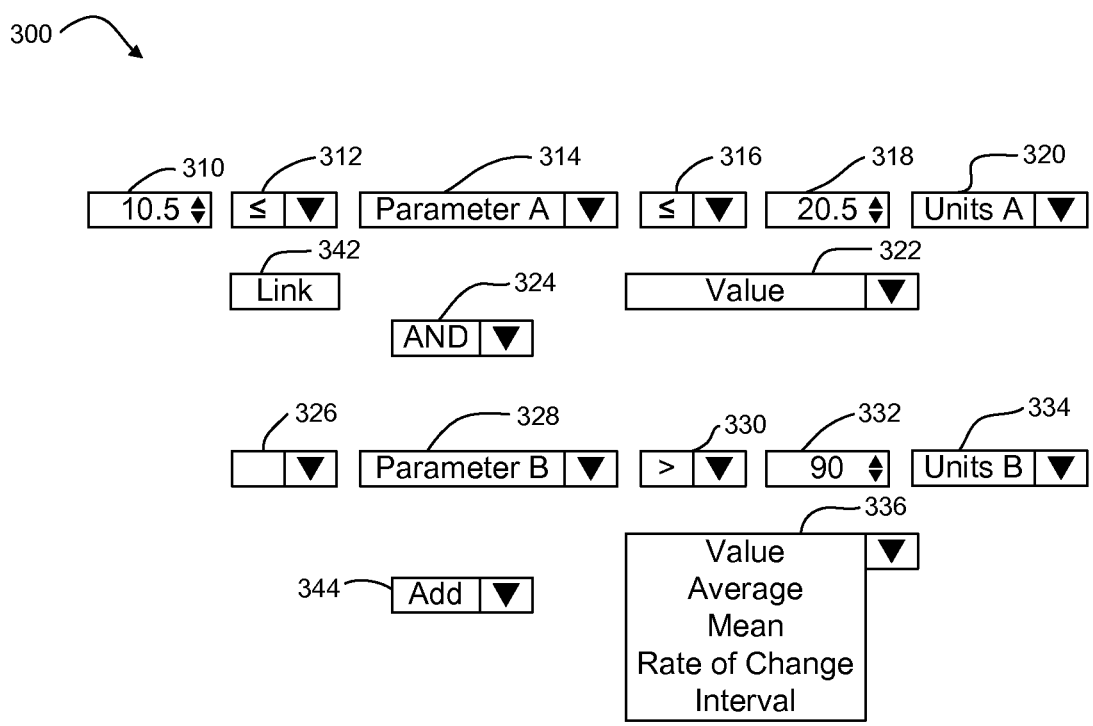
Figure 3E:
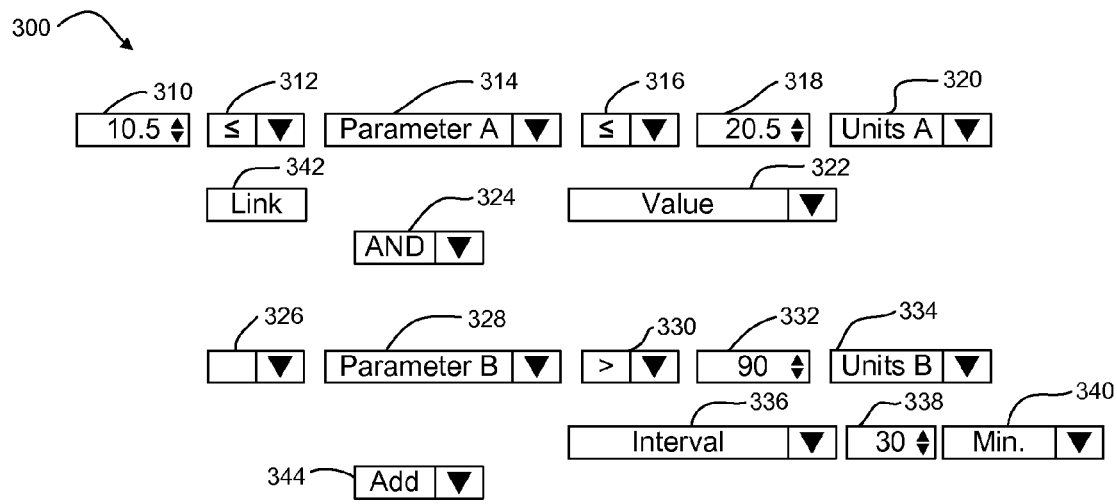

The logic connector field 324 allows the user to add another boundary condition by selecting a logic connector that relates the two boundary conditions. As shown in FIG. 3B, for example, the user may select from among the Boolean connectors "AND," "OR," or "NOT". As shown in FIGS. 3C, 3D, and 3E, the user in this example selects "AND" to connect the first boundary condition associated with Parameter A with a second boundary condition defined by the user-selectable fields 326, 328, 330, 332.

For the second boundary condition in this example, the user leaves the first comparator field 326 blank, which results in not displaying a corresponding limit field. The user selects "Parameter B" from the parameter field 328, greater than ($>$) from the second comparator field 330, and "90" in the limit field 332 to create the following expression for the second boundary condition:

$$\text{Parameter B} > 90. \tag{4}$$

As shown in FIG. 3D, the user also selects appropriate units from a units field 334 corresponding to the selected Parameter B. As shown in FIG. 3E, the user selects "Interval" from a parameter field 336 corresponding to the second boundary condition, which causes a time constant field 338 and a time units field 340 to be displayed to the user. In this example, the user specifies an interval of 30 minutes over which expression (4) is violated before triggering an alarm.

As shown in FIGS. 3C, 3D, and 3E, the user interface 300 also includes a link field 342. In this example, the user has not linked the first boundary condition (corresponding to Parameter A) to the second boundary condition (corresponding to Parameter B).

Upon making the selections shown in FIG. 3E, the user has defined an alarm condition that is a combination of expressions (3) and (4). In other words, the alarm is triggered when both expression (3) and expression (4) are violated.

Figure 3F:
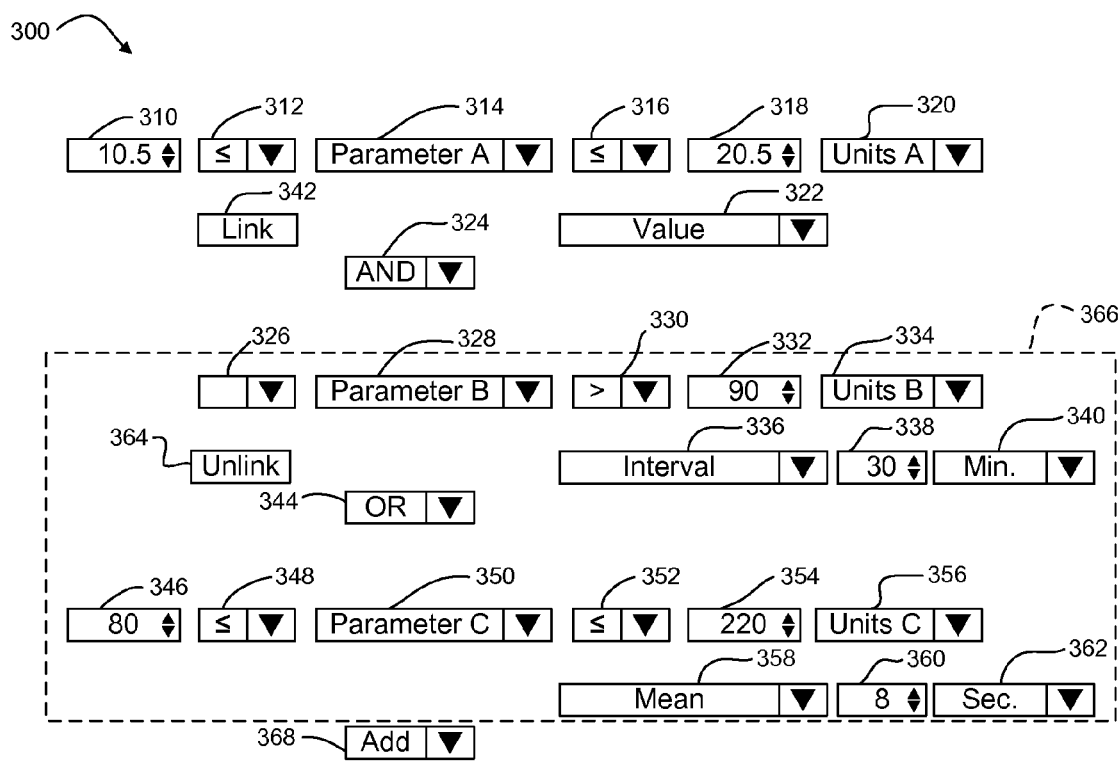

The user may add an additional boundary condition by selecting an option from a logic connector field 344. As shown in FIG. 3F, the user in this example selects "OR" from the logic connector field 344 and defines a third boundary condition using a first limit field 346, a first comparator field 348, a parameter field 350, a second comparator field 352, a second limit field 354, and a units field 356 to create the following expression:

$$80 \leq \text{Parameter C} \leq 220. \quad (5)$$

In this example, the user then selects "Mean" from a function field 358 corresponding to the third boundary condition, which indicates that a mean value of data associated with Parameter C is used to determine whether or not expression (5) is satisfied. A time constant field 360 and a time units field 362 allow the user to specify that the mean is determined using data collected over an 8 second interval.

The user also selects a link field 364 (which causes the displayed text to change from "link" to "unlink") to nest the second boundary condition (corresponding to Parameter B) and the third boundary condition (corresponding to Parameter C). As shown in FIG. 3F, the user interface 300 in certain embodiments includes markings 366 (e.g., the dashed box) to indicate the nested boundary conditions. The selected link field 364 indicates that the "OR" of the logic connector field 344 is executed before the "AND" of the logic connector field 324. In other words, the alarm is triggered when the first boundary condition is violated "AND" either the second boundary condition "OR" the third boundary condition is violated. Thus, expressions (3), (4), and (5) are combined as follows:

$$10.5 \leq \text{Parameter A} \leq 20.5$$

"AND"

$$(\text{Parameter B} > 90 \text{ "OR" } 80 \leq \text{Parameter C} \leq 220). \quad (6)$$

As shown in FIG. 3F, a new logic connector field 368 is added to the user interface 300 after each new boundary condition is defined to allow the user to add yet another boundary condition. Thus, the user may build customized alarms that include as many patient parameters as desired. Further, the user may rearrange the boundary conditions, logical connectors, and links to meet the monitoring needs of a particular patient or condition.

Figure 4:
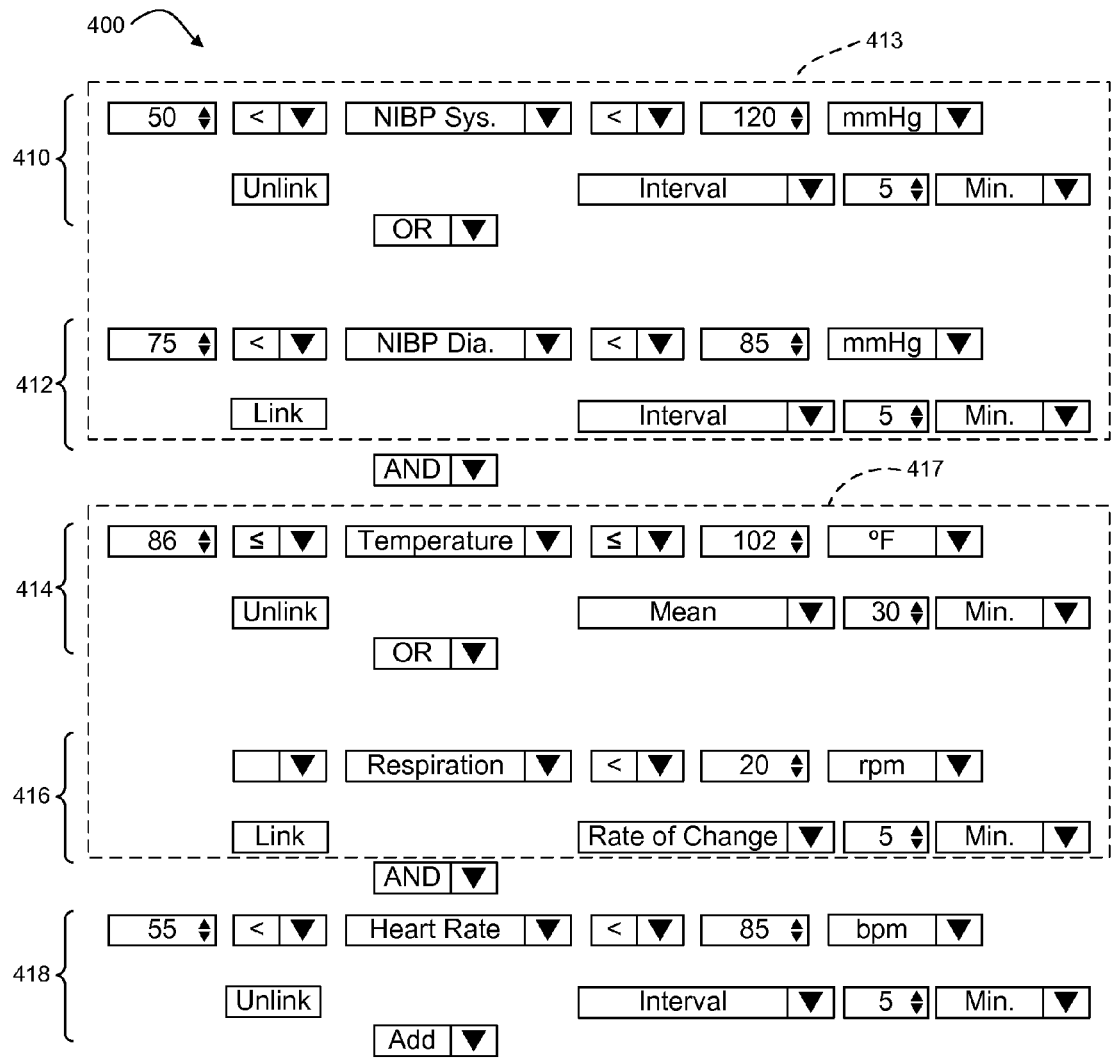
FIG. 4 graphically represents an example user interface configured by a user of a patient monitor according to one embodiment.

FIG. 4 graphically represents an example user interface 400 configured by a user of a patient monitor according to one embodiment. An artisan will recognize from the disclosure herein that the patient parameters, values, and units shown in FIG. 4 are provided by way of example only and not by limitation. In the example in FIG. 4, medical personnel configure the user interface 400 to create a custom alarm to detect the likely hood that a patient has a certain condition (e.g., that the patient has become septic). The alarm is based on a combination of blood pressure, temperature, respiration, and heart rate.

As shown in FIG. 4, the user defines a first boundary condition 410 related to systolic non-invasive blood pressure (NIBP Sys.) in units of millimeter of Mercury (mmHG) according to the following expression:

$$50 \text{ mmHG} < \text{NIBP Sys.} < 120 \text{ mmHG}, \quad (7)$$

where expression (7) is violated when the limits are exceeded for more than 5 minutes. The first boundary condition 410 is associated with a second boundary condition 412 with a logical "OR" connector. The first boundary condition 410 is also linked to the second boundary condition 412, as indicated by that dashed box 413. The second boundary condition 412 is related to diastolic non-invasive blood pressure (NIBP Dia.) according to the expression:

$$75 \text{ mmHG} < \text{NIBP Dia.} < 85 \text{ mmHG}, \quad (8)$$

where expression (8) is violated when the limits are exceed for more than 5 minutes.

A third boundary condition 414 and a fourth boundary condition 416 are also nested together, as indicated by the dashed box 417. The third boundary condition 414 is related to temperature according to the following expression:

$$86° \text{ F.} \leq \text{Temperature} \leq 102° \text{ F.}, \quad (9)$$

where expression (9) is violated if the mean temperature over a 30 minute period exceeds the limits. The third boundary condition 414 is associated with the fourth boundary condition 416 with a logical "OR" connector. The fourth boundary condition 416 is related to respiration in units of respirations per minute (rpm) according to the expression:

$$\text{Respiration} < 20 \text{ rpm}, \quad (10)$$

where the expression (10) corresponds to a rate of change in the patient's respiration over a 5 minute time interval. In other words, expression (10) is violated when the patient's respiration rate changes by more than 20 rpm in 5 minutes.

A fifth boundary condition 418 is related to heart rate measured in beats per minute (bpm) according to the expression:

$$55 \text{ bpm} < \text{Heart Rate} < 85 \text{ bmp}, \quad (11)$$

where the expression (11) is violated if the limits are exceeded by more than 5 minutes.

The first nested boundary conditions 410, 412, the second nested boundary conditions 414, 416, and the fifth boundary condition are associated with one another through "AND" logical connectors. Thus, the combination of expressions (7) -(11) may be represented as:

(50 mmHG<NIBP Sys.<120 mmHG "OR" 75 mmHG<NIBP Dia.<85 mmHG)

"AND"

(86° F.≤Temperature≤102° F. "OR" Respiration<20 rpm)

"AND"

$$55 \text{ bpm} < \text{Heart Rate} < 85 \text{ bmp}. \quad (12)$$

Thus, the user can configure a custom alarm for any type of condition or combination of patient parameters.

Figure 5:
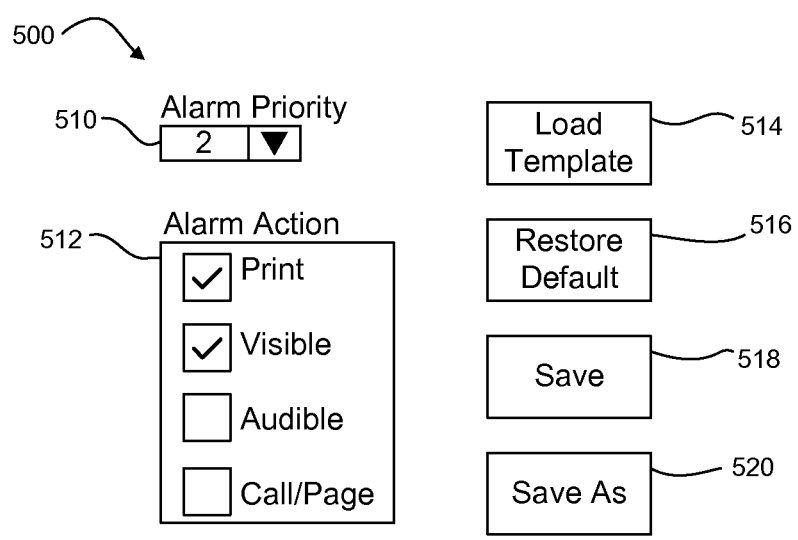
FIG. 5 graphically represents a user interface for auxiliary alarm functions according to one embodiment.

The user may be also allowed to configure other types of options with respect to an alarm. For example, FIG. 5 graphically represents a user interface 500 for auxiliary alarm functions according to one embodiment. The user interface 500 includes an alarm priority field 510 that allows the user to specify a priority level for the alarm with respect to other alarms. The user interface 500 also includes an alarm action field 512 that allows the user to select one or more responses to a triggered alarm such as printing associated data, providing visible indicia of the alarm (e.g., a flashing light), providing audible indicia of the alarm, calling and/or paging a doctor, nurse, or other personnel, or other suitable actions. Default alarm actions may be based on the alarm priority.

The user interface 500 also includes a load template field 514 that allows the user to load an alarm template associated with a particular patient or condition. The user interface 500 may also include a restore default field 516 to reset the alarm conditions for the patient monitor, or for a particular alarm profile or template, to a predetermined set of conditions and limit values. The user interface 500 may also include fields 518, 520 for saving a modified or new alarm, alarm template, or alarm profile. The fields 518, 520 may also allow the user to name or rename an alarm, alarm template, or alarm profile. Upon pressing the "save as" field 520, for example, the user may be allowed to name a new alarm "Septic" so that an alarm call displays a "Septic" message.

Figure 6A:
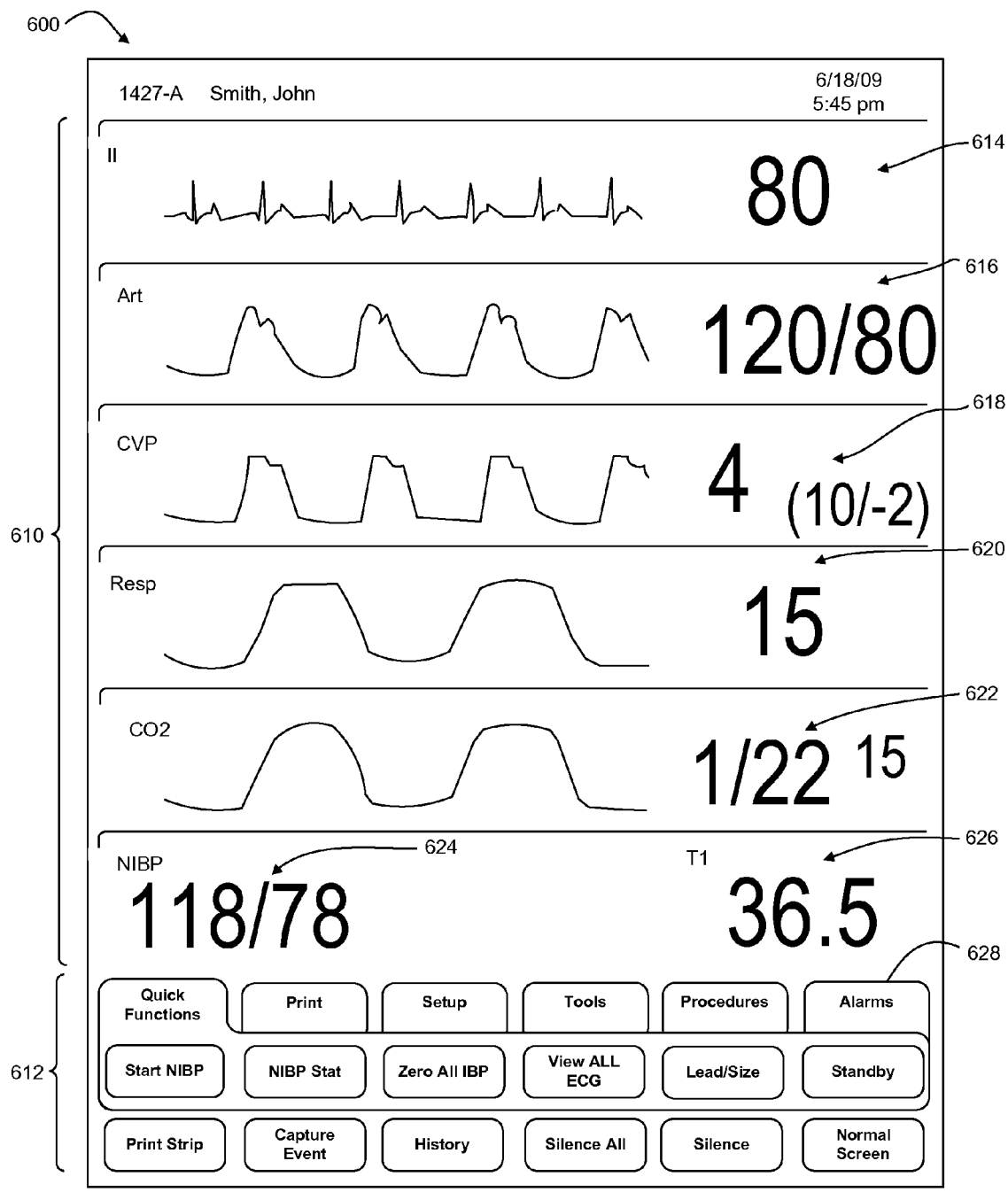
FIGS. 6A and 6B illustrate example user interfaces that may be used according to one embodiment.
Figure 6B:
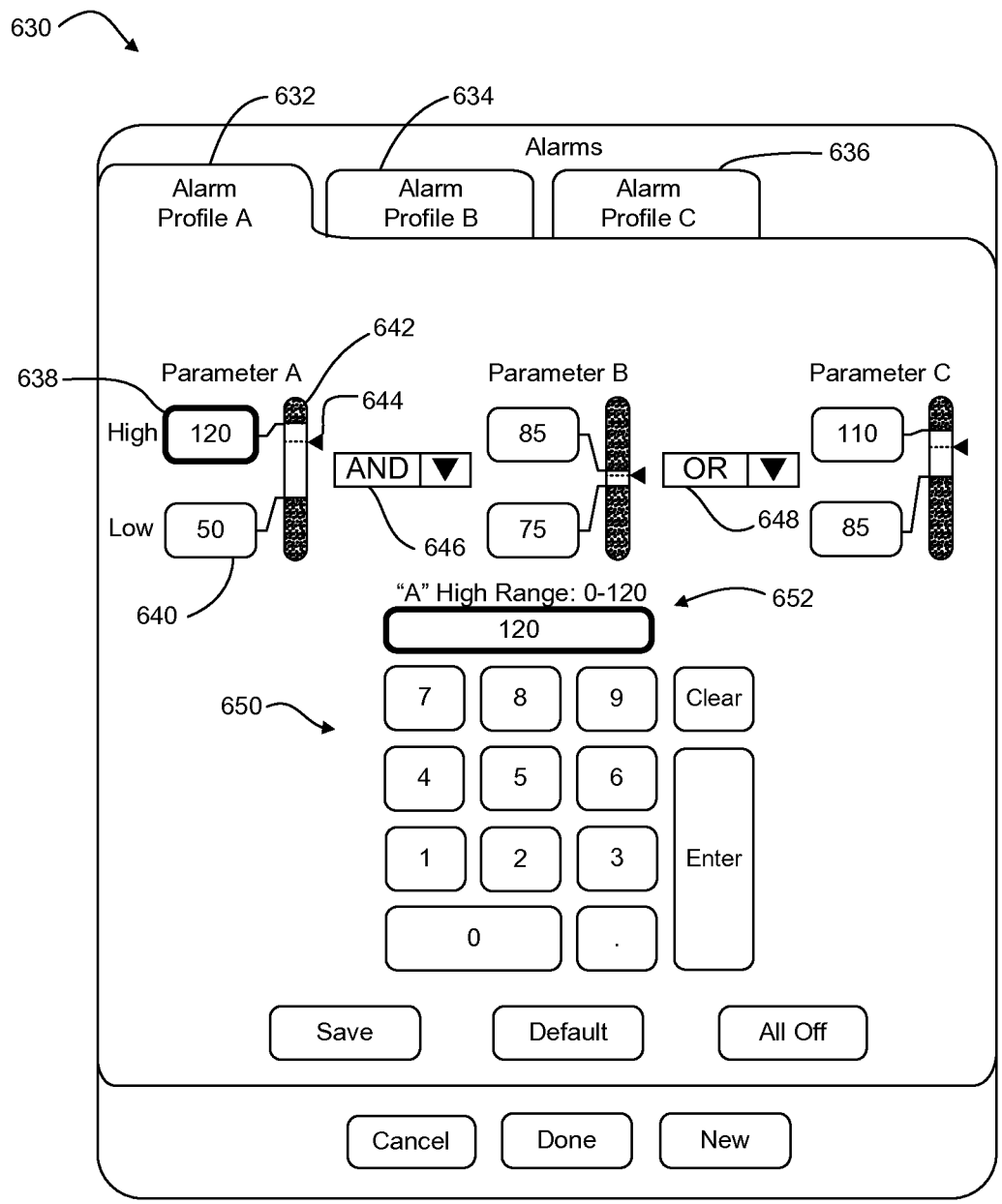

An artisan will recognize from the disclosure herein that the embodiments are not limited to the types of formats of the user interfaces 300, 400, 500 discussed above. Indeed, any user interface may be used that allows a user to define boundary conditions associated with different patient parameters and provide logic connectors between the different boundary conditions. For example, FIGS. 6A and 6B illustrate example user interfaces that may be used according to one embodiment. In FIG. 6A, a user interface 600 for a patient monitor includes a first area 610 for displaying monitored patient data and a second area 612 for displaying controls and functions used to control and configure the patient monitor.

As shown in FIG. 6A, the first area 610 may display (e.g., graphically and numerically) information associated with a plurality of different patient parameters including electrocardiogram (ECG) information 614 (e.g., received through lead II), arterial pressure information 616, central venous pressure (CVP) information 618, respiration information 620, carbon dioxide ($CO_2$) level information 622, non-invasive blood pressure (NIBP) information 624, and temperature information 626. An artisan will understand from the disclosure herein that many other types of patient parameter information may also be displayed.

The second area 612 of the user interface 600 includes, among other tabs and controls, an alarms tab 628. When the user selects the alarms tab 628, according to one embodiment, the patient monitor displays the user interface 630 shown in FIG. 6B to the user. As shown in FIG. 6B, the user interface 630 includes a plurality (three shown) of alarm profile tabs 632, 634, 636. Each alarm profile tab 632, 634, 636 may correspond to a different monitoring situation, patient, patient condition, user preference, ward or hospital preference, and/or device default alarm condition.

The alarm profile tab 632 (for profile "A") includes user-selectable fields for Parameter A, Parameter B, and Parameter C. For example, Parameter A is associated with a high limit field 638 and a low limit field 640. The user interface 630 also displays a meter 642 associated with Parameter A. The meter 642 graphically indicates the values of entered into the high and low limit fields 638, 640 with respect to a current value indicator 644. Similar fields and meters are associated with Parameter B and Parameter C.

The alarm profile tab 632 also includes a first logic connector field 646 and a second logic connector field 648. The first logic connector field 646 relates the user-defined boundary condition associated with Parameter A to the user-defined boundary condition associated with Parameter B. The second logic connector field 648 relates the user-defined boundary condition associated with Parameter B to the user-defined boundary condition associated with Parameter C. Although not shown, the user interface 630 may also provide a field to link or nest multiple boundary conditions, as discussed above. In other embodiments, the boundary conditions may be executed in a predetermined order (e.g., from left to right).

In certain embodiments, as shown in FIG. 6B, the user interface 630 also includes a numeric keypad 650 for entering limit values. The user may select numerical values with the numeric keypad 650 using, for example, a mouse or a touch-screen. The numeric keypad 650 may be associated with an indicator 652 that displays a value being entered for a selected field. In some embodiments, the indicator 652 also displays a recommended range for the selected field. In the example shown in FIG. 6B, the high limit field 638 associated with Parameter A is currently selected. Thus, the indicator 652 shows a recommended range of "0-120" for Parameter A. In some embodiments, the user interface 630 warns the user if the entered value is not within the recommended range. In other embodiments, the user interface 630 prevents the user from entering a value that is not within the recommended range. Accordingly, the recommended range may be a default setting or may be set by a supervisor or hospital administrator. In certain embodiments, as discussed above, the user interface also allows the user to name or rename an alarm, alarm template, or alarm profile (e.g., upon pressing a "Save" button).

An artisan will recognize that the embodiments are not limited to the example user interfaces illustrated in FIGS. 3A, 3B, 3C, 3D, 3E, 3F, 4, 5, 6A, and 6B. Indeed, any user interface may be used that allows a user to customize multi-parameter alarms for particular patients and/or medical conditions by selecting patient parameters, desired levels or limits, comparators, and logic connectors to define an alarm condition. A user interface (not shown) in one embodiment, for example, uses a toolbar approach where elements such as patient parameters, logic connectors (AND, OR), rate change, and other elements discussed herein are provided in a user-selectable toolbar. In such an embodiment, the user may drag a patient parameter from the toolbar onto a screen. The user may then apply rate changes or comparators to the selected patient parameter. The user may also drag multiple patient parameters from the toolbar onto the screen and then connect them with logical operators. The user may save the alarm with a name that the system displays when the selected alarm conditions are met.

It is often desirable to continuously monitor patient parameters when transporting patients, including while transporting patients between hospital wards. Transporting patients between hospital wards, however, may require nurses or other hospital staff to spend time and effort reattaching the patient from a fixed monitoring system to a portable monitoring system and/or reconfiguring a patient monitor with configuration settings, including alarm settings, used by the different wards. The patient monitor configuration settings may be defined by administrators of each ward and may be based on hospital-specific practices and/or general (e.g., statewide or nationwide) standard practices. For example, an emergency room may be required to set different alarms, monitor a different set of patient parameters, or use different display settings (e.g., brightness or colors) than that of a catheterization lab or an intensive care unit.

Thus, when a portable patient monitor is introduced into a patient ward, the patient monitor generally needs to be configured for that particular ward's custom settings. This may be accomplished, for example, by accessing the patient monitor's menu system and configuring the patient monitor. Alternatively, the patient monitor may be configured by downloading a configuration from an external storage device or from a network. The configuration process can be time consuming. If it is required to manually load the configuration data from a storage device or a network, the user may forget to load the configuration data and the patient monitor will not be set to the ward's custom configuration. If the user is required to enter the configuration data manually into the patient monitor, the configuration process may also be error prone.

Thus, in one embodiment, a ward's custom configuration is associated with a docking station. For example, in one embodiment, the ward's custom configuration settings may be stored in a memory device in the docking station. Upon connection to the docking station, the patient monitor may load some or all of the ward's custom configuration settings from the memory device. In another embodiment, the docking station may be associated with a unique identifier. Upon connection to the docking station, the monitor may establish a connection with a network and download some or all of the ward's custom configuration settings from a server based on the unique identifier.

Because a user (e.g., a nurse) may spend a substantial amount of time configuring a patient monitor with custom settings for a particular patient, it may be undesirable for some or all of the settings to be automatically updated to the default configuration settings of a new ward. For example, when a patient is transported from an operating recovery room to an intensive care unit, the user may want to keep at least some of the settings configured in the operating recovery room based on the particular patient's condition. Thus, whenever a user connects a patient monitor to a docking station in a new ward according to certain embodiments, the patient monitor prompts the user to change the monitor's settings to the new ward's default settings. If the user indicates that an update to the new ward's default settings is desired, the monitor automatically loads the new ward's default settings (e.g., from either the docking station or a network server) and configures itself according to the loaded settings. In certain such embodiments, the user may select only a portion of the new ward's default settings, while maintaining other current settings. Because the update to the new ward's default settings is not automatic, a user may selectively maintain all or part of a custom configuration previously established for a particular patient.

In addition, or in other embodiments, certain docking stations are associated with transient locations, such as a radiology department, where a patient may be expected to remain for a relatively short period of time before returning to his or her room or before being transported to another area of the hospital. In such embodiments, the patient monitor is configured to determine whether or not a currently connected docking station is a transient docking station. If the patient monitor determines that the currently connected docking station is a non-transient docking station associated with default configuration settings, then the patient monitor prompts the user to update the monitor's settings with the default settings associated with the ward of the currently connected docking station. If, however, the patient monitor determines that the currently connected docking station is a transient docking station, the monitor does not prompt the user to update the patient monitor's settings with those associated with the currently connected docking station, if any. In some embodiments, transient docking stations are not associated with a set of default monitor settings.

The patient monitor configuration settings may include, for example, multi-parameter alarm profiles (as discussed above), selection of displayed waveforms, waveform display priority, display layout including definitions of hot keys or user configuration buttons, waveform colors, speaker volume, and/or brightness.

Figure 7:
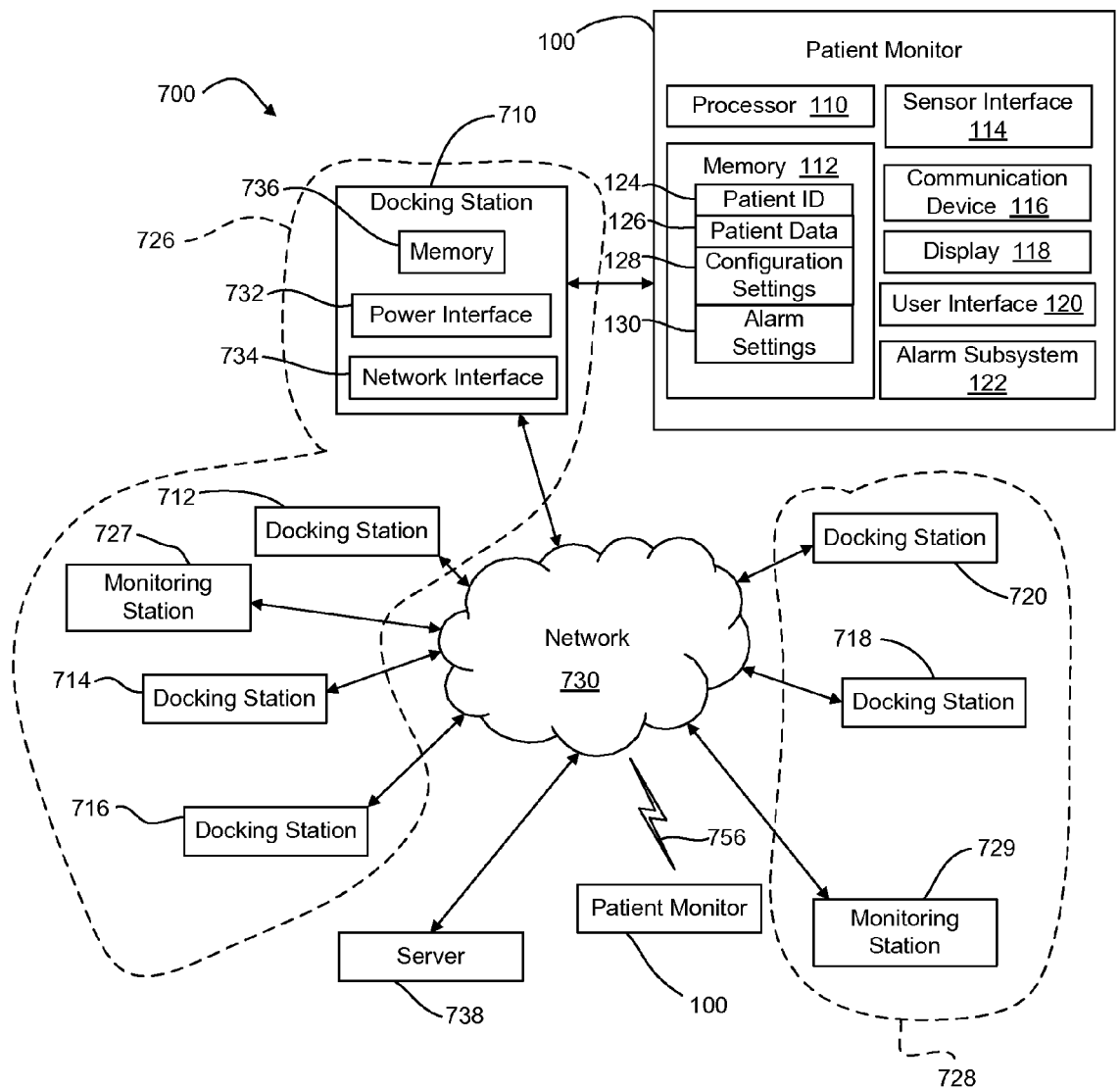
FIG. 7 is a block diagram of a patient monitoring system according to one embodiment.

FIG. 7 is a block diagram of a patient monitoring system 700 according to one embodiment. The patient monitoring system 700 includes a plurality of docking stations 710, 712, 714, 716, 718, 720, and one or more patient monitors 100 (two shown), such as the patient monitor 100 shown in FIG. 1. In the example embodiment shown in FIG. 7, the docking stations 710, 712, 714 are associated with a first patient monitoring location 726, and the docking stations 718, 720 are associated with a second patient monitoring location 728. The first and second patient monitoring locations 726, 728 may be different hospital wards. For example, the first or second patient monitoring locations 726, 728 may correspond to surgery, day surgery, urology, respiratory, transplant, dialysis, renal, oncology, radiology, catheterization, or any other ward, unit, or department of the hospital. A first monitoring station 727 may be used to remotely monitor patients in the first patient monitoring location 726 and a second monitoring station 729 may be used to remotely monitor patients in the second patient monitoring location 728. The first patient monitoring location 726 is associated with a first set of default configuration settings and the second patient monitoring location 728 is associated with a second set of default configuration settings. In this example embodiment, the first set of default configuration settings is different than the second set of default configuration settings. Further, at least one of the first and second set of default configuration settings includes a default multi-parameter alarm profile that the user may customize, as discussed above.

The patient monitors 100 are mobile to allow patients to be continuously monitored during transportation between the first and second patient monitoring locations 726, 728 without being disconnected from the respective patient monitor 100. Accordingly, the patient monitors 100 are each configured to be selectively coupled with and selectively decoupled from any of the respective docking stations 710, 712, 714, 716, 718, 720.

For illustrative purposes, the patient monitor 100 is shown as being coupled to the docking station 710. In certain embodiments, the docking stations 710, 712, 714, 716, 718, 720 provide the respective patient monitors 100 with power and/or a connection to a network 730, such a hospital's local area network (LAN) and/or the Internet. Accordingly, the docking station 710 is illustrated as including a power interface 732 and a network interface 734. The power interface 732 may be configured to convert an alternating current (AC) power signal to a direct current (DC) power signal and/or provide power signal conditioning for the coupled patient monitor 100. The network interface 734 may include, for example, an Ethernet communication controller to allow the coupled patient monitor 100 to communicate through the network 730 through the docking station 710.

The network interface 734 may be associated with a media access control (MAC) address.

In certain embodiments, the docking station 710 may also include a memory device 736. The memory device 736 may include non-volatile random access memory (RAM) that provides addressable storage and may be used in certain embodiments to store the default configuration settings associated with the first patient monitor location 726. In addition, or in other embodiments, the memory device 736 stores a unique identifier associated with the first patient monitoring location 726. The patient monitor 100 reads the unique identifier from the memory device 736. In one embodiment, the patient monitor 100 includes a radio frequency identification (RFID) (not shown) for reading the unique identifier from the docking station 710. In other embodiments, the patient monitor 100 directly accesses an addressable memory location in the memory device 736 of the docking station 710 to access the unique identifier. The patient monitor 100 then transmits the unique identifier to a server 738 through the network interface 734. In response, the server 738 transmits the default configuration settings corresponding to the first patient monitoring location 726 to the patient monitor 100 through the network interface 734. In certain such embodiments, the server 738 also stores the default configuration settings in the memory device 736 as a backup in case communication through the network is lost or is temporarily unavailable. Although the memory device 736 is illustrated in FIG. 7 as a separate unit, an artisan will recognize from the disclosure herein that the network interface may include memory for storing a unique identifier such as a MAC address.

The patient monitor 100 may store the patient data signals in the memory device 112 along with other data. For example, the patient monitor 100 may store a current set of configuration settings in the memory device 112. In one embodiment, the patient monitor 100 replaces the current set of configuration settings in the memory device 112 with the default configuration settings corresponding to the first patient monitoring location 726 received from the memory device 736 of the docking station 710 or from the server 738. In another embodiment, the patient monitor 100 maintains the current set of configuration settings as it stores the default configuration settings for the first patient monitoring location 726 in a different memory location in the memory device 112. Thus, the user can select which set of stored configuration settings to use. In one embodiment, the set of configuration settings maintained in the memory device 112 includes default settings used by the patient monitor 100.

The communication device 116 is configured to communicate with the network 730 through the network interface 734 of the docking station 710. In certain embodiments, the communication device 116 is also configured to wirelessly communicate with the network 730 (see element 756) when the patient monitor 100 is not coupled to any of the docking stations 710, 712, 714, 716, 718, 720.

The processor 110 is configured to detect a coupling of the patient monitor 100 to the docking station 710. In response to a predetermined condition, the processor 110 prompts the user (e.g., through the user interface 120) to select one or more of the default configuration settings associated with the first patient monitoring location 726. In response to user selections through the user interface 120, the processor 110 loads the selected default configuration settings into the memory device 112 and configures the patient monitor 100 accordingly.

The predetermined condition may include a determination by the processor 110 that the first patient monitor location 726 is a non-transient hospital ward. For example, the first patient monitor location 726 may be an intensive care unit where the patient is expected to remain for a period of hours or days. The processor 110 may be further configured to detect that the patient monitor 100 has been coupled to the transient docking station 716. In response to the determination of the transient location, the processor 110 may maintain a current set of configuration settings in disregard to one or more default settings, if any, associated with the transient patient monitor location. When the patient monitor 100 is coupled to the transient docking station, the user is not prompted to change the patient monitor's current set of configuration settings. Thus, the user (e.g., a nurse) in a particular ward does not need to worry about the settings being changed when, for example, the patient is sent for chest x-rays.

In addition, or in other embodiments, the predetermined condition may include a determination by the processor 110 that a current set of configuration settings is different than the default configuration settings associated with the first patient monitor location 726. Thus, the user is not prompted to change settings when the patient monitor changes docking stations within the same patient monitoring location (e.g., the patient is assigned a different bed within the same ward), or when the patient monitor is transported between patient monitoring locations that have the same default configuration settings.

The predetermined condition may also include a determination by the processor 110 that one or more of the default configuration settings associated with the first patient monitoring location 726 are optional settings. Thus, the user is not prompted and the default configuration settings are automatically loaded when all of the default configurations settings are required (e.g., by an administrator over the first patient monitoring location 726).

Further, the predetermined condition may include a determination by the processor 110 that the current settings include an unprotected setting that conflicts with one or more default configuration settings. For example, a current set of configuration settings may be protected such that a sufficient authorization level is required (e.g., by an administrator or supervisor) to change or ignore the protected settings. If a current setting is protected, then the user is not prompted to change the setting.

Figure 8:
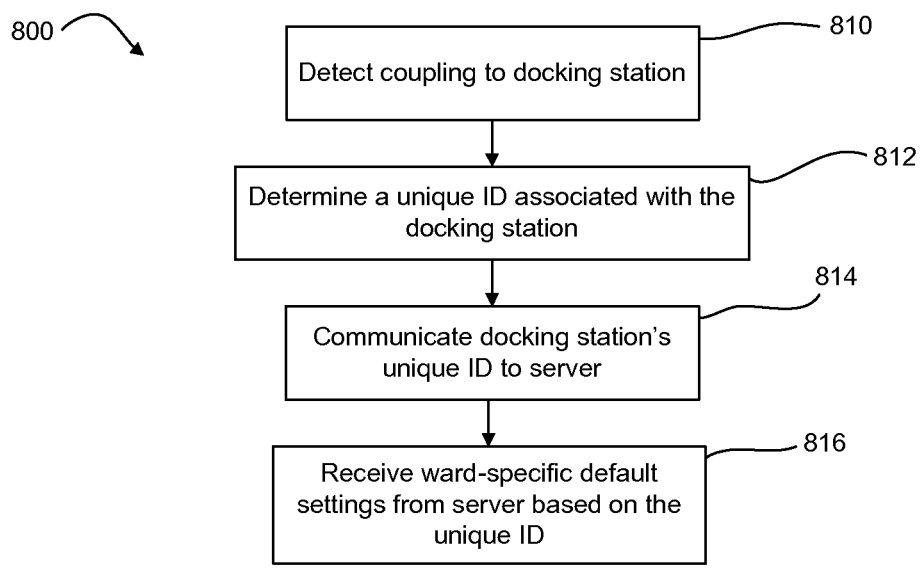
FIG. 8 is a flowchart of a process for updating the configuration settings of a patient monitor from a network server according to one embodiment.

FIG. 8 is a flowchart of a process 800 for updating the configuration settings of a patient monitor from a network server according to one embodiment. The process 800 includes detecting 810 a coupling of the patient monitor to a docking station and determining 212 a unique identifier (ID) associated with the docking station. As discussed above, the unique ID may be stored in the docking station's memory and/or may be a MAC address. The process 800 further includes communicating 814 the docking station's unique ID to the network server and receiving 816 ward-specific default settings from the server based on the unique ID.

Figure 9A:
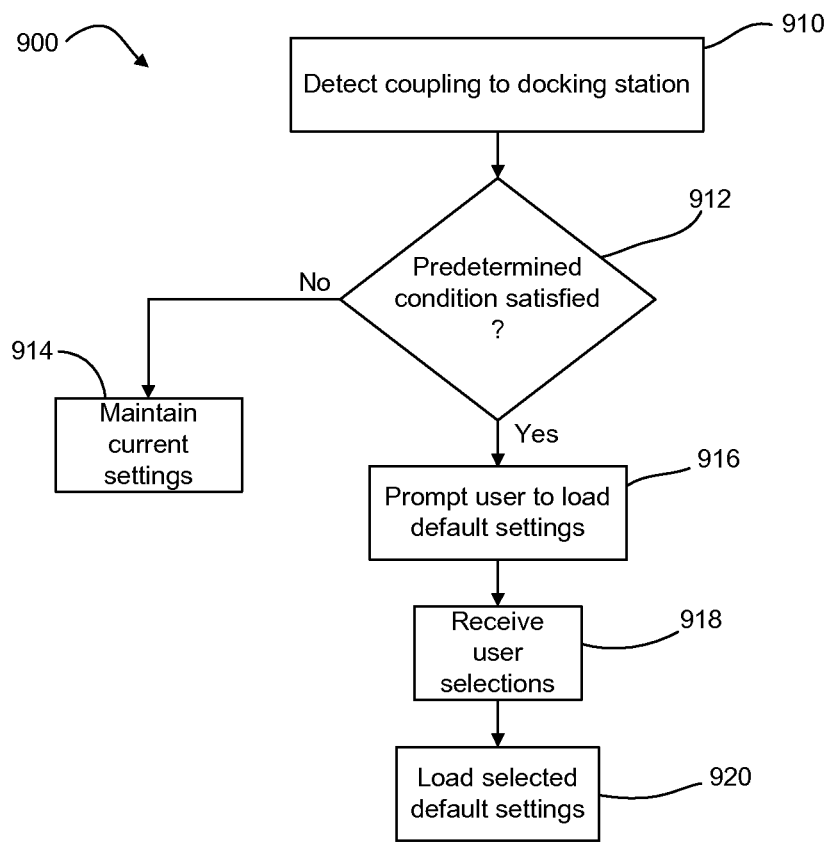
FIG. 9A is a flowchart of a method for use in a portable patient monitoring system according to one embodiment.

FIG. 9A is a flowchart of a method 900 for use in a portable patient monitoring system according to one embodiment. The method 900 includes detecting 910 a coupling of a portable patient monitor to a docking station and querying 912 whether a predetermined condition has been satisfied. If the predetermined condition has not been satisfied, the method 900 includes maintaining 914 the current settings of the patient monitor. If, however, the predetermined conditions have been satisfied, the method 900 includes prompting 916 a user to load default settings associated with a patient monitoring location of the docking station. The method 900 further includes receiving 918 user selections indicating which, if any, of the default settings to use, and loading 920 the selected default settings into the patient monitor.

Figure 9B:
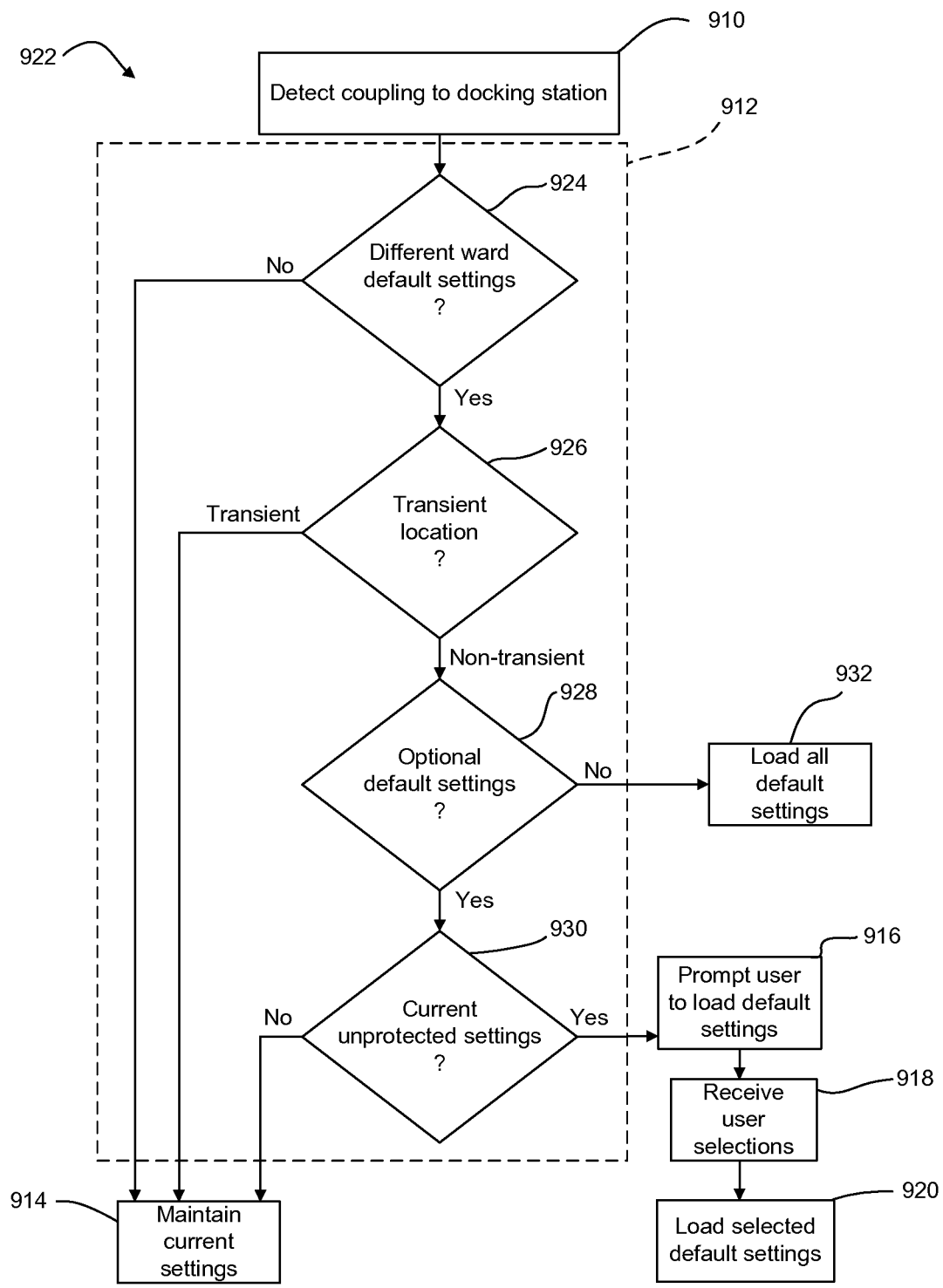
FIG. 9B is a flowchart of a method for use in a portable patient monitoring system according to other embodiments.

FIG. 9B is a flowchart of a method 922 for use in a portable patient monitoring system according to other embodiments. As discussed above with respect to the method 900 of FIG. 9A, the method 922 shown in FIG. 9B includes detecting 910 a coupling of a portable patient monitor to a docking station. In the method 922 shown in FIG. 9B, however, illustrates various options for querying 912 whether a predetermined condition has been satisfied. One or more of the different illustrated options 924, 926, 928, 930 may be used in any combination. For example, the method 922 may include querying 924 whether different ward default settings are required as compared to a current set of default settings in the patient monitor. If the ward default settings are not different than the current set of settings in the patient monitor, then the method 922 includes maintaining 914 the current settings of the patient monitor.

The method may also include querying 926 whether the coupled docking station corresponds to a transient location. If the coupled docking station is a transient location, the method 922 includes maintaining 914 the current settings of the patient monitoring system. If the coupled docking station is a non-transient location, the method 922 proceeds toward prompting 916 the user to load the default settings. The method 922 may also include querying 928 whether there are any optional default settings corresponding to the patient monitoring location. If none of the default settings for the patient monitoring location are optional, the method 922 includes loading 932 all of the default settings without prompting the user. The method 922 may also include querying 930 whether any of the current settings are unprotected. If all of the current settings are protected, then the method 922 includes maintaining 914 the current settings of the patient monitoring system. If, on the other hand, one or more of the current settings are unprotected, then the method 922 includes prompting 916 the user to load the default settings. The method 922 further includes receiving 918 user selections indicating which, if any, of the default settings to use, and loading 920 the selected default settings into the patient monitor.

It will be understood by those having skill in the art that many changes may be made to the details of the above-described embodiments without departing from the underlying principles of the invention. The scope of the present invention should, therefore, be determined only by the following claims.

The invention claimed is:

1. A method for monitoring a patient using user-customizable alarm profiles in a patient monitor system, the method comprising:
providing a user interface to a user of the patient monitor system for the selection of a multi-parameter alarm condition based on measured values associated with a combination of multiple patient parameters;
receiving, through the user interface, a first boundary condition associated with a first patient parameter selected by the user, the first patient parameter corresponding to a plurality of measured values of a first type of monitored patient physiological data received through a sensor interface of the patient monitor system;
receiving, through the user interface, a second boundary condition associated with a second patient parameter selected by the user, the second patient parameter corresponding to a plurality of measured values of a second type of monitored patient physiological data received through the sensor interface of the patient monitor system, wherein the second type of monitored patient physiological data is different from the first type of monitored patient physiological data;
receiving, through the user interface, a first logic connector that relates the first boundary condition of the first patient parameter to the second boundary condition of the second patient parameter to define the multi-parameter alarm condition;
measuring, with the patient monitor system, values of the first patient parameter and the second patient parameter; and
triggering an alarm based on the measured values, the first boundary condition, the second boundary condition, and the defined multi-parameter alarm condition.

2. The method of claim 1, further comprising:
receiving, through the user interface, a selection of the first patient parameter from among a plurality of available patient parameters; and
receiving, through the user interface, a selection of the second patient parameter from among the plurality of available patient parameters.

3. The method of claim 1, wherein receiving the first boundary condition comprises:
receiving, through the user interface, a selection of a first comparator from among a plurality of available comparators; and
receiving, through the user interface, a selection of a first limit value associated with the first patient parameter and the first comparator.

4. The method of claim 3, wherein receiving the first boundary condition further comprises:
receiving, through the user interface, a selection of a second comparator from among the plurality of available comparators; and
receiving, through the user interface, a selection of a second limit value associated with the first patient parameter and the second comparator.

5. The method of claim 1, further comprising:
receiving, through the user interface, a third boundary condition associated with a third patient parameter; and
receiving, through the user interface, a second logic connector that relates the third boundary condition to at least one of the first boundary condition and the second boundary condition to further define the alarm condition.

6. The method of claim 5, further comprising:
receiving, through the user interface, an indication of a link between at least one of the first boundary condition, the second boundary condition, and the third boundary condition,
wherein the link defines an order in which to process the first logic connector and the second logic connector to determine an occurrence of the defined alarm condition.

7. The method of claim 1, wherein receiving the first boundary condition comprises:
receiving, through the user interface, a limit value and a time constant, wherein the time constant defines an interval over which the measured values of the first patient parameter exceed the limit value before triggering the alarm.

8. The method of claim 1, wherein receiving the first boundary condition comprises:

receiving, through the user interface, a limit value defining a rate of change for the first patient parameter.

9. The method of claim 1, wherein receiving the first boundary condition comprises:
receiving, through the user interface, a limit value and an indication of a statistical operation, wherein the statistical operation defines an analysis to perform on the measured values of the first patient parameter.

10. A patient monitor comprising:
a processor;
a sensor interface to receive and process patient physiological data signals corresponding to measured patient parameters;
a display device to display the patient physiological data signals and a user interface for allowing the user to customize multi-parameter alarm profiles; and
an alarm subsystem configured to:
receive, through the user interface, a first boundary condition associated with a first patient parameter selected by the user corresponding to a first type of patient physiological data signal comprising measured values received through the sensor interface;
receive, through the user interface, a second boundary condition associated with a second patient parameter selected by the user corresponding to a second type of patient physiological data signal comprising measured values received through the sensor interface, wherein the second type of patient physiological data signal is distinct from the first type of patient physiological data signal;
receive, through the user interface, a first logic connector that relates the first boundary condition of the first patient parameter to the second boundary condition of the second patient parameter to define a multi-parameter alarm condition; and
trigger an alarm based on the measured first and second patient parameters with the defined multi-parameter alarm condition.

11. The patient monitor of claim 10, wherein the alarm subsystem is further configured to:
receive, through the user interface, a selection of the first patient parameter from among a plurality of available patient parameters; and
receive, through the user interface, a selection of the second patient parameter from among the plurality of available patient parameters.

12. The patient monitor of claim 10, wherein to receive the first boundary condition the alarm subsystem is further configured to:
receive, through the user interface, a selection of a first comparator from among a plurality of available comparators; and
receive, through the user interface, a selection of a first limit value associated with the first patient parameter and the first comparator.

13. The patient monitor of claim 12, wherein to receive the first boundary condition the alarm subsystem is further configured to:
receive, through the user interface, a selection of a second comparator from among the plurality of available comparators; and
receive, through the user interface, a selection of a second limit value associated with the first patient parameter and the second comparator.

14. The patient monitor of claim 10, wherein the alarm subsystem is further configured to:
receive, through the user interface, a third boundary condition associated with a third patient parameter; and
receive, through the user interface, a second logic connector that relates the third boundary condition to at least one of the first boundary condition and the second boundary condition to further define the alarm condition.

15. The patient monitor of claim 14, wherein the alarm subsystem is further configured to:
receive, through the user interface, an indication of a link between at least one of the first boundary condition, the second boundary condition, and the third boundary condition,
wherein the link defines an order in which to process the first logic connector and the second logic connector to determine an occurrence of the defined alarm condition.

16. The patient monitor of claim 10, wherein to receive the first boundary condition the alarm subsystem is further configured to:
receive, through the user interface, a limit value and a time constant, wherein the time constant defines an interval over which the measured values of the first patient parameter exceed the limit value before triggering the alarm.

17. The patient monitor of claim 10, wherein to receive the first boundary condition the alarm subsystem is further configured to:
receive, through the user interface, a limit value defining a rate of change for the first patient parameter.

18. The patient monitor of claim 10, wherein to receive the first boundary condition the alarm subsystem is further configured to:
receive, through the user interface, a limit value and an indication of a statistical operation, wherein the statistical operation defines an analysis to perform on the measured values of the first patient parameter.

19. A non-transitory computer-readable storage medium having stored thereon computer-executable instructions for performing operations for monitoring a patient using user-customizable multi-parameter alarm profiles in a patient monitor system, the operations comprising:
displaying a user interface to a user of the patient monitor system;
receiving, through the user interface, a first boundary condition associated with a first patient parameter selected by the user, the first patient parameter corresponding to measured values of a first type of monitored patient physiological data received through a sensor interface;
receiving, through the user interface, a second boundary condition associated with a second patient parameter selected by the user, the second patient parameter corresponding to measured values of a second type of monitored patient physiological data received through the sensor interface of the patient monitor system, wherein the second type of monitored patient physiological data is different from the first type of monitored patient physiological data;
receiving, through the user interface, a first logic connector that relates the first boundary condition of the first patient parameter to the second boundary condition of the second patient parameter to define a multi-parameter alarm condition;
measuring, with the patient monitor system, values of the first patient parameter and the second patient parameter; and triggering an alarm based on the measured values, the first boundary condition, the second boundary condition, and the defined multi-parameter alarm condition.

20. The non-transitory computer-readable storage medium of claim 19, the operations further comprising:
receiving, through the user interface, a third boundary condition associated with a third patient parameter; and
receiving, through the user interface, a second logic connector that relates the third boundary condition to at least one of the first boundary condition and the second boundary condition to further define the alarm condition.

21. The non-transitory computer-readable storage medium of claim 20, the operations further comprising:
receiving, through the user interface, an indication of a link between at least one of the first boundary condition, the second boundary condition, and the third boundary condition,
wherein the link defines an order in which to process the first logic connector and the second logic connector to determine an occurrence of the defined alarm condition.

22. A system for monitoring patients using user-customizable multi-parameter alarm profiles, the system comprising:
means for receiving a first boundary condition associated with a first patient parameter, the first patient parameter selected by the user and corresponding to measured values of a first type of monitored patient physiological data received through a sensor interface of the patient monitor system;
means for receiving a second boundary condition associated with a second patient parameter, the second patient parameter selected by the user and corresponding to measured values of a second type of monitored patient physiological data received through the sensor interface of the patient monitor system, wherein the second type of monitored patient physiological data is different from the first type of monitored patient physiological data;
means for receiving a first logic connector that relates the first boundary condition of the first patient parameter to the second boundary condition of the second patient parameter to define the multi-parameter alarm condition;
means for measuring values of the first patient parameter and the second patient parameter; and
means for triggering an alarm based on the measured values, the first boundary condition, the second boundary condition, and the defined multi-parameter alarm condition.

* * * * *